United States Patent
Tschudi et al.

(10) Patent No.: US 6,785,407 B1
(45) Date of Patent: Aug. 31, 2004

(54) FINGERPRINT SENSOR

(75) Inventors: Jon Tschudi, Oslo (NO); Ib-Rune Johansen, Oslo (NO); Ivar Mathiassen, Narvik (NO); Svein Mathiassen, Heggedal (NO)

(73) Assignee: Idex AS, Heggedal (NO)

( * ) Notice: Subject to any disclaimer, the term of this patent is extended or adjusted under 35 U.S.C. 154(b) by 0 days.

(21) Appl. No.: 09/622,940

(22) PCT Filed: Feb. 4, 1999

(86) PCT No.: PCT/NO99/00038

§ 371 (c)(1),
(2), (4) Date: Oct. 12, 2000

(87) PCT Pub. No.: WO99/43258

PCT Pub. Date: Sep. 2, 1999

(30) Foreign Application Priority Data

Feb. 26, 1998 (NO) .................................. 980827

(51) Int. Cl.[7] .............................................. G06K 9/00
(52) U.S. Cl. ....................................................... 382/124
(58) Field of Search ................. 382/115–116, 126–127; 902/3–6; 235/380, 382, 382.5; 340/5.53, 5.83; 356/71, 73

(56) References Cited

U.S. PATENT DOCUMENTS

| | | |
|---|---|---|
| 4,353,056 A | 10/1982 | Tsikos |
| 4,394,773 A | 7/1983 | Ruell |
| 4,429,413 A | 1/1984 | Edwards |
| 4,784,484 A | 11/1988 | Jensen |
| 5,325,442 A | 6/1994 | Knapp |
| 5,503,029 A | 4/1996 | Tamori |
| 5,559,504 A | 9/1996 | Itsumi et al. |
| 5,828,773 A | 10/1998 | Setlak et al. |
| 5,841,888 A | 11/1998 | Setlak et al. |
| 5,845,005 A | 12/1998 | Setlak et al. |
| 5,852,670 A | 12/1998 | Setlak et al. |
| 5,862,248 A | 1/1999 | Salatino et al. |
| 5,903,225 A | 5/1999 | Schmitt et al. |
| 5,920,640 A | 7/1999 | Salatino et al. |
| 5,940,526 A | 8/1999 | Setlak et al. |
| 5,953,441 A | 9/1999 | Setlak |
| 5,956,415 A | 9/1999 | McCalley et al. |
| 5,963,679 A | 10/1999 | Setlak |
| 6,144,757 A * | 11/2000 | Fukuzumi .................. 382/124 |
| 6,154,580 A * | 11/2000 | Kuriyama et al. .......... 382/312 |
| 6,289,114 B1 * | 9/2001 | Mainguet ................... 382/124 |

FOREIGN PATENT DOCUMENTS

| | | |
|---|---|---|
| JP | 8154921 | 6/1996 |
| JP | 10-003532 | 1/1998 |
| JP | 10-222641 | 8/1998 |
| WO | WO 86/06266 A1 | 11/1986 |
| WO | WO 96/32061 A1 | 10/1996 |

* cited by examiner

*Primary Examiner*—Vikkram Bali
(74) *Attorney, Agent, or Firm*—Rothwell, Figg, Ernst & Manbeck, P.C.

(57) ABSTRACT

This invention relates to an apparatus for measuring structures in a fingerprint or the like, comprising at least one sensor array adapted to be positioned close to, or in contact with, the surface of the fingerprint, the sensor array being adapted to measure chosen characteristics of the surface, e.g. by measuring capacitance or resistivity, at a plurality of positions. At least one sensor array comprises at least one line of sensors, adapted to measure said characteristics at chosen intervals of time, the surface having a relative movement in relation to the sensor array with a direction essentially perpendicular to the at least one line of sensors, and at least one of the outer ends of at least one sensor array protrudes towards the surface to be measured, providing an essentially U-shaped cross section in a plane perpendicular to the direction of said movement.

15 Claims, 2 Drawing Sheets

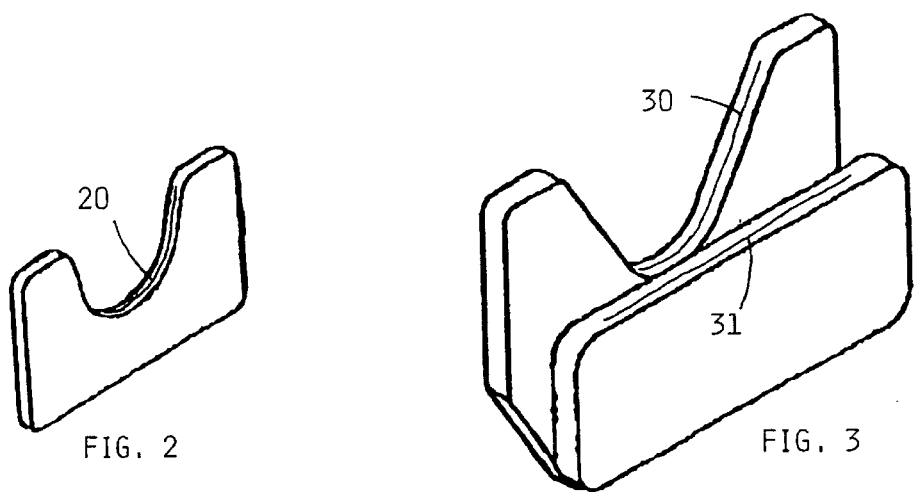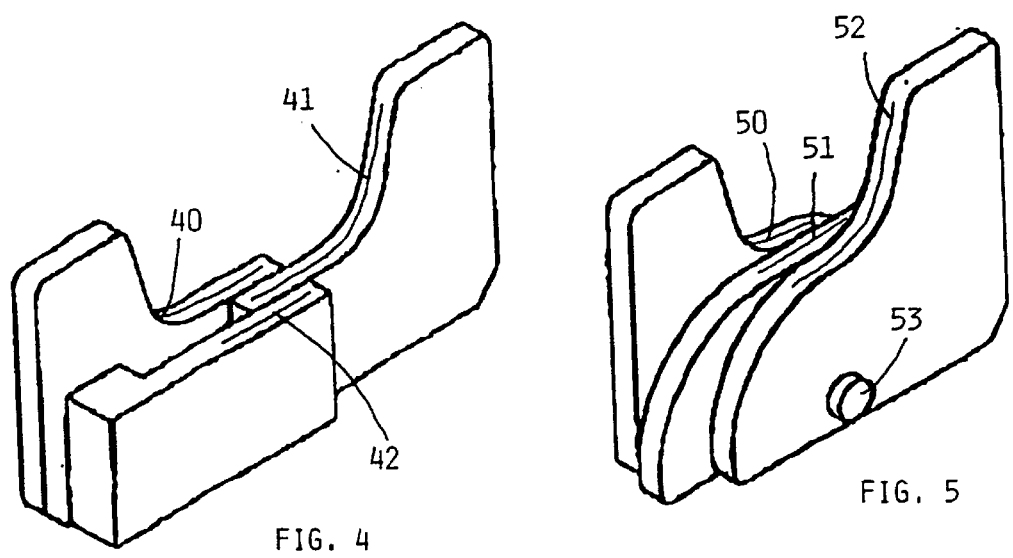

FINGERPRINT SENSOR

BACKGROUND

1. Field of the Invention

The invention relates to a method and an apparatus for the measuring of structures in a fingerprint or the like, comprising the measuring of chosen characteristics of the surface of the fingerprint, e.g. capacitance or resistivity, using a sensor array comprising a plurality of sensors, positioned in contact with, or close to, the surface.

2. Description of the Related Art

Identification by the use of fingerprints has lately come to the fore as a result of the increasing needs for security relating to, for example, credit cards or computer systems as well as the greatly increased availability of pattern recognition algorithms. Some systems for recognition of fingerprints have already been made available on the market. The techniques used to register the fingerprint vary.

Some of the previously known solutions are based upon optical technology using light with one or more wavelengths. These are sensitive to dirt and contamination, both in the fingerprint and on the sensor surface, and thus cleaning is necessary for both.

Another alternative is pressure measurement, such as is described in U.S. Pat. No. 5.559.504, U.S. Pat. No. 5.503.029 and U.S. Pat. No. 4.394.773. This, however, has the disadvantage that the sensor surface becomes sensitive to mechanical wear and damage, as the sensor has to have an at least partially compliant surface.

Temperature sensors have also been suggested, for example in U.S. Pat. No. 4,429,413 and international patent application PCT/NO96/00082.

Fingerprint sensors may be exposed to long term use under varying and sometimes demanding conditions. The sensor therefore needs to have a robust surface and to be as insensitive to pollution in the fingerprint and on the sensor as possible. It must be capable of reading most fingerprints without being disturbed by latent prints from earlier use, and also be capable of imaging so-called "dry fingers" that represent a problem for optical sensors. In some cases, e.g. in credit cards or computer keyboards, it would also be advantageous if the sensor could be made compact.

In the view of costs there is also a demand for simplicity and minimizing of the number of parts.

It is an object of the present invention to provide a sensor being easy to produce, making them cheap in production, and also relatively small.

In addition to the solutions mentioned above the measuring of capacitance has been tried as a method to measure finger prints. Examples are shown in U.S. Pat. No. 4.353.056 and U.S. Pat. No. 5.325.442. While the ridges of the fingerprint touch the sensor surface the valleys have a small distance to the sensor surface, resulting in a difference in capacitance and/or conduction measured at the different sensors. Humidity may affect the measurements, but if it is evenly distributed throughout the fingerprint an analysis of the contrast between the measurements can provide a picture of it.

All the solutions mentioned above are based upon two-dimensional sensor arrays with dimensions comparable to the size of the fingerprint. These are expensive and difficult to produce, since they comprise a large number of sensors simultaneously measuring the surface.

Also, the known sensors disclose only flat sensor surfaces. As finger prints are curved surfaces the sensors are only capable of measuring a small part of the finger print, and are thus sensitive to the angle with which the fingerprint is held against the surface.

SUMMARY OF THE INVENTION

The present invention provides a method and an apparatus for the measuring of structures in a fingerprint or the like, for example using one of the techniques described above, and characterized as stated in the disclosed claims.

As the surface of the sensor array is small, and contains few sensors compared to the known solutions, it is inexpensive and relatively simple to make. As the fingerprint to be measured is moved past the sensor array it is selfcleaning and there is no latent fingerprint remaining from the previous user, giving another advantage in relation to the known finger print sensors.

The curved or essentially U-shaped line of sensors may be made in one piece or by combining two or three linear sensor arrays. Examples of such linear arrays are described in EP 735.502.

Since the details in the fingerprints are small, it is also difficult to make the sensors of the detector small enough. In a preferred embodiment the apparatus and method according to the invention comprises two or more parallel lines of measuring points, each line of measuring points being shifted in the longitudinal direction with a distance less than the distance between the measuring points, the sensor array comprising two or more parallel lines of equally spaced sensors, preferably shifted in the longitudinal direction of the sensor array. This provides a possibility to measure structures in the fingerprint smaller than the spacing of the sensors. This is not possible with any of the previously known detector systems.

Thus, it is to be understood that the term "essentially one-dimensional array" here refers to an array having a length being much larger than its width, and may comprise more than one line of sensors.

DESCRIPTION OF THE DRAWINGS

The invention will be described below with reference to the enclosed drawings, which illustrate one possible embodiment of the invention.

FIG. 2 shows a perspective view of a first embodiment of the invention.

FIG. 3 shows a perspective view of a second embodiment of the invention.

FIG. 4 shows a perspective view of a third embodiment of the invention.

FIG. 5 shows a perspective view of a fourth embodiment of the invention.

DETAILED DESCRIPTION

Figure 1A:
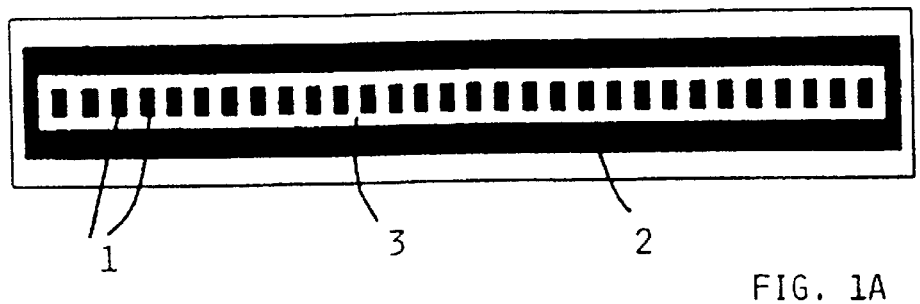
FIGS. 1a and 1b show schematic views of two versions of the sensor lines.

In FIG. 1a a single, linear array of sensors 1 is shown. The sensors may be of different kinds, such as pressure sensors or temperature sensors, but preferably they are electrical conductors providing a possibility to measure conduction, impedance or capacitance of the different parts of the fingerprint. The surface to be measured is moved in a perpendicular direction relative to the line of sensors. such as epoxy. In the shown embodiment an electrically conducting material 2 surrounds the sensors which may be used to provide a reference potential. If capacitance is to be measured the conductors are covered by an insulating through the fingerprint, between the each of the sensors 1 and the surrounding reference level may be measured.

Figure 1B:
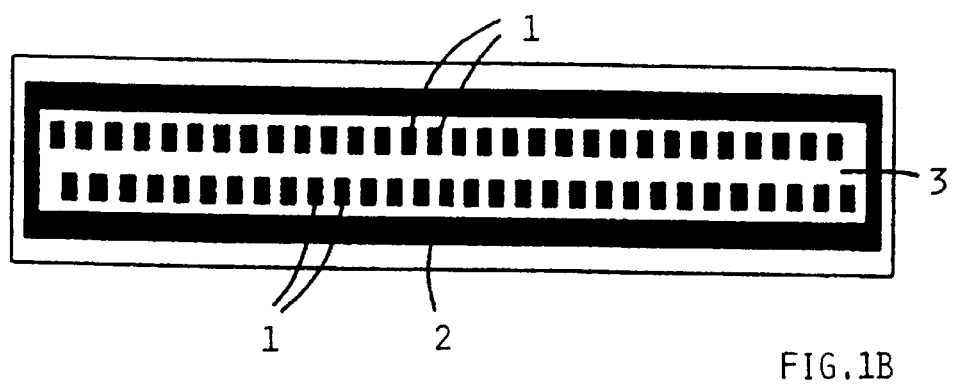

To measure the structures in a fingerprint the array will typically be 10–15 mm long with a resolution of 50 μm. This is difficult or expensive to obtain using a single line of sensors. FIG. 1b shows a preferred embodiment of the invention in which the sensor array comprises two lines of sensors 1 being slightly shifted in relation to each other. When moving a surface across the sensor array the measurements of each of the sensors in the second line will fall between the measured point of the first line, providing the required resolution with a larger distance between the sensors. Three or more lines are possible to improve the resolution even more, but more than five would be impractical because of the distance between the lines and the resulting time lapse between the measurements of the first and the last line. Also, an apparatus using many lines would be sensitive to the direction in which the finger is moved.

When using a sensor array comprising two or more sensor lines, as shown in FIG. 1b, the measurements of the different lines must be combined to provide a signal corresponding to one single line of sensors. To do this the signals from the sensors must be adjusted for the time delay between the signals from the sensors in different lines. To do this the movement of the finger in relation to the sensor array must be known, either by moving the finger or sensor array with a chosen speed, or by measuring the movement of the finger.

Instead of using two or more continuous lines of sensor elements the sensor elements may be positioned in groups measuring features in chosen areas of the fingerprint, e.g. depending on the required security of the system or the available data.

Also, the velocity of the fingerprint in relation to the sensor may be measured by single, independent sensor elements positioned in the direction of the movement of the fingerprint. The velocity may be found by correlating similar features measured at different times at different sensor elements.

A detailed description of the sensor lines may be found in Norwegian Patent application No. 97.2759 (corresponding to international publication no. WO 98/58342). The solution therein using a number of conductors being connected to a microchip provides a preferred embodiment of the sensor arrays in the invention. The conductors stretch from the microchip to the sensors surface, so that their ends constitute the sensor elements.

FIG. 2 shows the most simple embodiment of the invention, in which the sensor array 20 has a U-shaped surface, the curvature of which is adapted to the dimensions of the finger to be measured. This solution provides measurements of a larger area of the finger print surface than known devices, linear or flat, but it has the disadvantage that the curvature is fixed, while the dimensions of fingers vary from person to person. Also, the sensor should be able to measure the prints of any finger of a person, to provide redundancy, e.g. in case of accidents.

One way to overcome this problem may be to attach the sensor array to a flexible material, taking shape after the finger.

In FIG. 3 another fixed solution is shown, comprising a first, slightly more V-shaped sensor array 30, and also comprising a second, linear sensor array 31 being positioned a chosen distance from the first array 30. In this case the U-shaped sensor array will image the sides of the finger, while the flat sensor will image the base of the finger. The two sensor arrays will of course measure partially the same part of a finger print. Correlating these sets of data may be used to find the velocity of the finger over the sensor arrays, as the distance between them is known.

A more flexible solution is shown in FIG. 4, comprising two sensor arrays 40,41, together defining a U-shape. The parts 40,41 are flexibly connected to each other allowing for a relative movement between them. The connection between the parts may be spring loaded, so that they follow the shape of the finger, or may be locked in a position chosen according to the size of the user's finger. The relative position between the parts 40,41 may be monitored to ease the data processing when combining the signal from the sensor arrays.

The embodiment shown in FIG. 4 may also comprise a third sensor array 42. As in the embodiment shown in FIG. 3 the distance between the sensor arrays and correlating of the signals to find the time lapse between the passing of the same features, may be used to find the velocity of the finger drawn through the fingerprint sensor.

A similar embodiment is shown in FIG. 5, where the parts 50,51,52 are rotated in relation to each other, around an axis 53. Again, the relative angle between the sensor parts may be measured to aid the combining of the measured data to obtain a representation of the fingerprint. In an alternative embodiment the intermediate part 51 may be omitted.

In all of the shown embodiments the sensor arrays may comprise a single line of sensor elements, as shown in FIG. 1a, or two or more, preferably shifted, lines of sensor elements, as indicated in FIG. 1b.

This invention provides a sensor apparatus being simple to produce using standard techniques, and thus cheap. It is also compact and rugged. If the used measuring technique is based on conductivity the sensor is durable, as the sensors, which in this case are the same as the conductors, will not change their characteristics as they and the surrounding epoxy are worn down. If capacitance is to be measured the conductors are covered by an insulating, durable layer.

The preferred layout of the sensor also allows the resolution to be better than the distance between the sensors, reducing cross-talk between the sensors.

In order to control the movement of the fingers the sensor may comprise grooves with a direction essentially perpendicular to the at least one line of sensors, corresponding to the direction of said movement between the sensor array and the finger print. The grooves will thus guide the finger and avoid movements in a direction other than the required direction.

The method and apparatus according to the invention may of course be utilized in many different ways, and different characteristics may be measured in order to provide a representation of the measured surface, in addition to capacitance and/or conductivity. Optical detectors may be used, and preferably transmitters, so that the reflected image of the fingerprint may be analysed regarding for example contrast and/or colour.

The sensors may, as mentioned above simply be the ends of conductors connected to means for measuring capacitance and/or conductivity, or may be sensors made from semiconducting materials. A preferred semiconducting material when cost is essential would be silicon.

Another possible embodiment within the scope of this invention comprises sensor lines of not equally spaced sensors positioned to measure chosen parts of the fingerprint.

What is claimed is:

1. Apparatus for measuring structures in a fingerprint comprising at least one sensor array adapted to be positioned close to, or in contact with, the surface of the fingerprint, the sensor array being adapted to measure chosen characteristics of the surface, by measuring capacitance or resistivity, at a plurality of positions, the at least one sensor array being an essentially one dimensional sensor array comprising at least one line of sensors, wherein the sensors are adapted to measure said characteristics at chosen intervals of time, the surface of the fingerprint having a relative movement in relation to the sensor array with a direction essentially perpendicular to the at least one line of sensors, the apparatus comprises means for combining the measurements at the different time intervals to obtain a segmented, two-dimensional representation of the characteristics of the surface of the fingerprint, and at least one of the outer ends of at least one sensor array protrudes towards the surface of the fingerprint to be measured, providing an essentially U-shaped cross section in a plane perpendicular to the direction of said movement.

2. Apparatus according, to claim 1, further comprising a furrow with an essentially U-shaped cross-section adapted to receive the finger, the at least one sensor array being provided at the surface of the furrow.

3. Apparatus according to claim 1, further comprising grooves with a direction essentially perpendicular to the at least one line of sensors, corresponding to the direction of said movement between the sensor array and the finger print, for guidance of the finger pulling direction.

4. Apparatus according to claim 1, the essentially one-dimensional sensor array comprising two or more parallel lines of essentially equally spaced sensors, shifted in the longitudinal direction of the sensor array with a distance not equal to the distance between the sensors.

5. Apparatus according to claim 1, further comprising measuring means for measuring of the movement of the surface in relation to the sensor array.

6. Apparatus according to claim 5, further comprising means for correlating the signals from the different lines of sensors to find the time lapse or special shift between the similar structures at the different sensor lines.

7. Apparatus according to claim 1, wherein the sensors are capacitive sensors adapted to measure variations in the capacitance along the sensor array.

8. Apparatus according to claim 1, wherein the sensors comprise electrodes being capable of measuring variations in the electric resistance along the sensor array.

9. Apparatus according to claim 1, wherein the sensor array is made from a semiconducting material, preferably silicon.

10. Apparatus according to claim 1, further comprising two or more sensor arrays being capable of moving in relation to each other.

11. Apparatus according to claim 1, wherein the sensor array is mounted in a flexible material.

12. Apparatus according to claim 1, wherein said sensor arrays comprise a first, generally U-shaped sensor array and a second, flat sensor array disposed adjacent said first sensor array.

13. Apparatus according to claim 1, wherein said sensor arrays comprise at least two sensor arrays, each of said two sensor arrays defining an opposite side of the U-shaped cross section, said two sensor arrays being flexibly connected to each other to allow relative movement between each of the two sensor arrays.

14. Apparatus according to claim 1, wherein said sensor arrays comprise two or more sensor arrays, each of said sensor arrays defining different portions of the U-shaped cross section, said sensor arrays being connected to each other so as to allow relative angular movement between the sensor arrays.

15. Apparatus according to claim 1, wherein said essentially U-shaped cross section is variable so as to accommodate fingers of varying sizes.

* * * * *